(12) United States Patent
Van Den Brink et al.

(10) Patent No.: US 7,888,102 B2
(45) Date of Patent: Feb. 15, 2011

(54) CELL LINE FOR PRODUCING CORONAVIRUSES

(75) Inventors: Edward Norbert Van Den Brink, Halfweg (NL); Jan Henrik Ter Meulen, Amsterdam (NL)

(73) Assignee: Crucell Holland B.V., Leiden (NL)

( * ) Notice: Subject to any disclaimer, the term of this patent is extended or adjusted under 35 U.S.C. 154(b) by 127 days.

(21) Appl. No.: 11/988,146

(22) PCT Filed: Jul. 21, 2006

(86) PCT No.: PCT/EP2006/064489

§ 371 (c)(1),
(2), (4) Date: Dec. 27, 2007

(87) PCT Pub. No.: WO2007/010028

PCT Pub. Date: Jan. 25, 2007

(65) Prior Publication Data

US 2009/0098530 A1    Apr. 16, 2009

(30) Foreign Application Priority Data

Jul. 22, 2005    (EP)    ................. 05106768

(51) Int. Cl.
*C12N 1/20* (2006.01)
*C12N 7/00* (2006.01)
(52) U.S. Cl. .................. 435/252.3; 435/235.1; 435/459
(58) Field of Classification Search ........................ None
See application file for complete search history.

(56) References Cited

U.S. PATENT DOCUMENTS

| 5,994,128 A | 11/1999 | Fallaux et al. | |
|---|---|---|---|
| 2003/0092160 A1* | 5/2003 | Bout et al. ............... | 435/235.1 |
| 2005/0069869 A1 | 3/2005 | Ambrosino et al. | |

FOREIGN PATENT DOCUMENTS

| EP | 1 054 064 | | 11/2000 |
|---|---|---|---|
| EP | 1 108 787 | A | 6/2001 |
| WO | WO 03/013599 | A2 | 2/2003 |
| WO | WO 2004/042042 | A | 5/2004 |
| WO | WO 2004/111081 | A3 | 12/2004 |
| WO | WO 2005/012337 | A2 | 2/2005 |
| WO | WO 2005/012338 | A1 | 2/2005 |
| WO | WO 2005/012360 | A2 | 2/2005 |
| WO | WO 2005/032487 | A | 4/2005 |
| WO | WO 2007/010028 | A1 | 1/2007 |

OTHER PUBLICATIONS

Li W, et al. "Angiotensin-converting enzyme 2 is a functional receptor for the SARS coronavirus." Nature. Nov. 27, 2003;426(6965):450-4.*
Office Action for U.S. Appl. No. 11/337,300, dated Jul. 9, 2009.
Office Action for U.S. Appl. No. 11/667,640, dated Jun. 25, 2009.
Cabezas et al., A structure-based approach to a synthetic vaccine for HIV-1, Biochemistry, Nov. 28, 2000, pp. 14377-14391, vol. 39, No. 47. Abstract.
Corapi et al., Localization of antigenic sites of the S glycoprotein of Feline Infectious Peritonitis Virus involved in neutralization and antibody-dependent enhancement, Journal of Virology, The American Society of Microbiology, May 1995, pp. 2858-2862, vol. 69, No. 5.
Ksiazek et al., A Novel Coronavirus Associated with Severe Acute Respiratory Syndrome, The New England Journal of Medicine, May 15, 2003, pp. 1953-1966, vol. 348, No. 20.
Li et al., The Structural Characterization and Antigenicity of the S Protein of SARS-CoV, Geno., Prot. & Bioinfo, May 2003, pp. 108-117, vol. 1, No. 2.
Lin et al., Identification of an epitope of SARS-coronavirus nucleocapsid protein, Cell Research, 2003, pp. 141-145, vol. 13, No. 3.
Marra et al., The genome sequence of the SARS-associated coronavirus, Science, May 30, 2003, pp. 1399-1404, vol. 300, No. 5624.
Posthumus et al., Analysis and Simulation of a Neutralizing Epitope of Transmissible Gastroenteritis Virus, Journal of Virology, Jul. 1, 1990, pp. 3304-3409, vol. 64, No. 7.
Rota et al., Characterization of a novel coronavirus associated with severe acute respiratory syndrome, Sciencexpress, May 2003, pp. 1-10, (visited Nov. 30, 2005), www.sciencexpress.org.
Thiel et al., Mechanisms and enzymes involved in SARS coronavirus genome expression, Journal of General Virology, 2003, pp. 2305-2315, vol. 84.
Vicenzi et al., Coronaviridae and SARS-associated Coronavirus Strain HSR1, Emerging Infectious Diseases, Mar. 2004, pp. 413-418, vol. 10, No. 3.
Database Entrez Nucleotides, online, NCBI, Apr. 21, 2003, Monroe et al., SARS coronavirus Urbani Strain, Database accession No. AY278741.
Database EMBL, Apr. 15, 2003, He et al., SARS coronavirus TOR2 complete genome, Database accession No. AY274119.
Database EMBL, Jun. 25, 2003, Vicenzi et al., SARS coronavirus HSR 1 complete genome, Database accession No. AY323977.
Database EMBL, online, Apr. 23, 2003, SARS coronavirus Urbani, complete genome, Database accession No. AY278741.
Database WPI, Section Ch, Week 200442, AN 2004-441790, Apr. 14, 2004.
Database WPI, Section Ch, Week 200432, AN 2004-341229, Feb. 4, 2004.
Database WPI, Section Ch, Week 200478, AN 2004-083758, Nov. 25, 2004.
PCT International Search Report, PCT/EP2004\051568, dated Aug. 22, 2005.
He et al., Antigenic and immunogenic characterization of recombinant baculovirus-expressed severe acute respiratory syndrome coronavirus spike protein: implication for vaccine design, J. Virol. Jun. 2006, pp. 5757-5767, vol. 80, No. 12.
Mitsuki et al., A single amino acid substitution in the S1 and S2 Spike protein domains determines the neutralization escape phenotype of SARS-CoV, Microbes Infect., Jul. 2008, pp. 908-915, vol. 10, No. 8, Epub Jun. 19, 2008.

(Continued)

*Primary Examiner*—Bo Peng
(74) *Attorney, Agent, or Firm*—TraskBritt (57) ABSTRACT

The invention relates to the production of coronaviruses. In particular, the invention relates to methods for producing SARS-CoV by using cells expressing a functional SARS-CoV receptor.

12 Claims, 1 Drawing Sheet

OTHER PUBLICATIONS

Yoo et al., A single amino acid change within antigenic domain II of the spike protein of bovine coronavirus confers resistance to virus neutralization, Clin Diagn Lab lmmunol. 2001, pp. 297-302, vol. 8, No. 2.

Keller et al., Passive immunity in prevention and treatment of infectious diseases, Clin. Microbiol. Rev., Oct. 2000, pp. 602-614, vol. 13, No. 4.

Cavanagh et al., Severe acute respiratory syndrome vaccine development: experiences of vaccination against avian infectious bronchitis coronavirus, Avian Pathology, Dec. 2003, pp. 567-582, vol. 32, No. 6.

Ter Meulen et al., Human monoclonal antibody as prophylaxis for SARS coronavirus infection in ferrets, Lancet, 2004, pp. 2139-2141, vol. 363.

Weiss et al., Coronavirus pathogenesis and the merging pathogen severe acute respiratory syndrome coronavirus, Microbiol. Mol. Biol. Rev. 2005, pp. 635-664, vol. 69, No. 4.

PCT International Preliminary Report on Patentability, PCT/EP2005/055876, dated Feb. 16, 2007.

PCT International Search Report, PCT/EP2005/055876, dated Mar. 3, 2006.

Bisht et al., Severe acute respiratory syndrome coronavirus spike protein expressed by attenuated vaccinia virus protectively immunizes mice, PNAS, Apr. 27, 2004, pp. 6641-6646, vol. 101, No. 17.

Bukreyev et al., Mucosal immunisation of African green monkeys (Cercopithecus aethiops) with an attenuated parainfluenza virus expressing the SARS coronavirus spike protein for the prevention of SARS, The Lancet, Jun. 26, 2004, pp. 2122-2127, vol. 363.

Sui et al., Potent neutralization of severe acute respiratory syndrome (SARS) coronavirus by a human mAb to S1 protein that blocks receptor association, PNAS, Feb. 24, 2004, pp. 2536-2541, vol. 101, No. 8.

Berry et al., Development and characterisation of neutralising monoclonal antibody to the SARS-coronavirus, Journal of Virological Methods, 2004, pp. 87-96, vol. 120.

Tirado et al., Antibody-Dependent Enhancement of Virus Infection and Disease, Viral Immunology, 2003, pp. 69-86, vol. 16, No. 1.

Wong et al., A 193-Amino Acid Fragment of the SARS Coronavirus S Protein Efficiently Binds Angiotensin-converting Enzyme 2, The Journal of Biological Chemistry, 2004, pp. 3197-3201, vol. 279, No. 5.

Van Den Brink et al., Molecular and Biological Characterization of Human Monoclonal Antibodies Binding to the Spike and Nucleocapsid Proteins of Severe Acute Respiratory Syndrome Coronavirus, Journal of Virology, Feb. 2005, pp. 1635-1644, vol. 79, No. 3.

Dionyssopoulou et al., Synthetic peptides as putative therapeutic agents in transplantation medicine: application of PEPSCAN to the identification of functional sequences in the extracellular domain of the interleukin-2 receptor beta chain (IL-2Rbeta), Journal of Immunological Methods, 2000, pp. 83-95, vol. 241.

Buchholz et al., Contributions of the structural proteins of severe acute respiratory syndrome coronavirus to protective immunity, PNAS, Jun. 29, 2004, pp. 9804-9809, vol. 101, No. 26.

Huang et al., Evaluation of Antibody Responses Against SARS Coronaviral Nucleocapsid or Spike Proteins by Immunoblotting or ELISA, J. Med. Virol., 2004, pp. 338-346, vol. 73., published online May 24, 2004.

Co-pending Cases U.S. Appl. No. 11/337,300, filed Jan. 20, 2006, Binding Molecules Against SARS-Coronavirus and Uses Thereof.

Co-pending Cases U.S. Appl. No. 11/667,640, filed May 11, 2007, Compositions Against SARS-Coronavirus and Uses Thereof.

Co-pending Cases U.S. Appl. No. 12/310,812, filed Mar. 6, 2009, Human Binding Molecules Capable of Neutralizing Influenza Virus H5N1 and Uses Thereof.

Hofmann et al., Human coronavirus NL63 employs the severe acute respiratory syndrome coronavirus receptor for cellular entry, PNAS, May 31, 2005, pp. 7988-7993, vol. 102, No. 22.

Hofmann et al., Susceptibility to SARS coronavirus S protein-driven infection correlates with expression of angiotensin converting enzyme 2 and infection can be blocked by soluble receptor, Biochemical and Biophysical Research Communications, 2004, pp. 1216-1221, vol. 319.

To et al., Exploring the pathogenesis of severe acute respiratory syndrome (SARS): the tissue distribution of the coronavirus (SARS-CoV) and its putative receptor, angiotensin-converting enzyme 2 (ACE2), Journal of Pathology, 2004, pp. 740-743, John Wiley & Sons, Ltd.

Mossel et al., Exogenous ACE2 Expression Allows Refractory Cell Lines To Support Severe Acute Respiratory Syndrome Coronavirus Replication, Journal of Virology, Mar. 2005, pp. 3846-3850, vol. 79, No. 6.

PCT International Search Report, PCT/EP2006/064489, dated Nov. 7, 2006.

PCT International Preliminary Report of Patentability, PCT/EP2006/064489, dated Oct. 30, 2007.

* cited by examiner

SEQUENCE LISTING

```
<160> NUMBER OF SEQ ID NOS: 4

<210> SEQ ID NO 1
<211> LENGTH: 805
<212> TYPE: PRT
<213> ORGANISM: Homo sapiens
```

<400> SEQUENCE: 1

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415
```

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
        450                 455                 460

Lys Gly Glu Ile Pro Lys Asp Gln Trp Met Lys Lys Trp Trp Glu Met
465                 470                 475                 480

Lys Arg Glu Ile Val Gly Val Val Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
            530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
            595                 600                 605

Asp Trp Ser Pro Tyr Ala Asp Gln Ser Ile Lys Val Arg Ile Ser Leu
            610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
            675                 680                 685

Lys Asn Val Ser Asp Ile Ile Pro Arg Thr Glu Val Glu Lys Ala Ile
            690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
            755                 760                 765

Lys Lys Lys Asn Lys Ala Arg Ser Gly Glu Asn Pro Tyr Ala Ser Ile
            770                 775                 780

Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 2
<211> LENGTH: 5549

<212> TYPE: DNA
<213> ORGANISM: Artificial sequence
<220> FEATURE:
<223> OTHER INFORMATION: pcDNA2004neo(-)

<400> SEQUENCE: 2

| | | | | | |
|---|---|---|---|---|---|
| gacggatcgg | gagatctccc | gatcccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgct | aggtggtcaa | tattggccat | tagccatatt | 240 |
| attcattggt | tatatagcat | aaatcaatat | tggctattgg | ccattgcata | cgttgtatcc | 300 |
| atatcataat | atgtacattt | atattggctc | atgtccaaca | ttaccgccat | gttgacattg | 360 |
| attattgact | agttattaat | agtaatcaat | tacgggtca | ttagttcata | gcccatatat | 420 |
| ggagttccgc | gttacataac | ttacggtaaa | tggcccgcct | ggctgaccgc | ccaacgaccc | 480 |
| ccgcccattg | acgtcaataa | tgacgtatgt | tcccatagta | acgccaatag | ggactttcca | 540 |
| ttgacgtcaa | tgggtggagt | atttacggta | aactgcccac | ttggcagtac | atcaagtgta | 600 |
| tcatatgcca | agtacgcccc | ctattgacgt | caatgacggt | aaatggcccg | cctggcatta | 660 |
| tgcccagtac | atgaccttat | gggactttcc | tacttggcag | tacatctacg | tattagtcat | 720 |
| cgctattacc | atggtgatgc | ggttttggca | gtacatcaat | gggcgtggat | agcggtttga | 780 |
| ctcacgggga | tttccaagtc | tccacccca t | tgacgtcaat | gggagtttgt | tttggcacca | 840 |
| aaatcaacgg | gactttccaa | aatgtcgtaa | caactccgcc | ccattgacgc | aaatgggcgg | 900 |
| taggcgtgta | cggtgggagg | tctatataag | cagagctcgt | ttagtgaacc | gtcagatcgc | 960 |
| ctggagacgc | catccacgct | gttttgacct | ccatagaaga | caccgggacc | gatccagcct | 1020 |
| ccgcggccgg | gaacggtgca | ttggaagctt | ggtaccggtg | aattcggcgc | gccgtcgacg | 1080 |
| atatcgatcg | gaccgacgcg | ttcgcgagcg | gccgcaattc | gctagcgtta | acggatcctc | 1140 |
| gagtctagag | tttaaaccgc | tgatcagcct | cgactgtgcc | ttctagttgc | cagccatctg | 1200 |
| ttgtttgccc | ctcccccgtg | ccttccttga | ccctggaagg | tgccactccc | actgtccttt | 1260 |
| cctaataaaa | tgaggaaatt | gcatcgcatt | gtctgagtag | gtgtcattct | attctggggg | 1320 |
| gtggggtggg | gcaggacagc | aagggggagg | attgggaaga | caatagcagg | catgctgggg | 1380 |
| atgcggtggg | ctctatggct | tctgaggcgg | aaagaaccag | ctggggctct | aggggggtatc | 1440 |
| cccacgcgcc | ctgtagcggc | gcattaagcg | cggcgggtgt | ggtggttacg | cgcagcgtga | 1500 |
| ccgctacact | tgccagcgcc | ctagcgcccg | ctcctttcgc | tttcttccct | tcctttctcg | 1560 |
| ccacgttcgc | cggctttccc | cgtcaagctc | taaatcgggg | catccctttta | gggttccgat | 1620 |
| ttagtgcttt | acggcacctc | gaccccaaaa | aacttgatta | gggtgatggt | tcacgtagtg | 1680 |
| ggccatcgcc | ctgatagacg | gtttttcgcc | ctttgacgtt | ggagtccacg | ttctttaata | 1740 |
| gtggactctt | gttccaaact | ggaacaacac | tcaacccta t | ctcggtctat | tcttttgatt | 1800 |
| tataagggat | tttggggatt | tcggcctatt | ggttaaaaaa | tgagctgatt | taacaaaaat | 1860 |
| ttaacgcgaa | ttaattctgt | ggaatgtgtg | tcagttaggg | tgtggaaagt | ccccaggctc | 1920 |
| cccaggcagg | cagaagtatg | caaagcatgc | atctcaatta | gtcagcaacc | aggtgtggaa | 1980 |
| agtccccagg | ctccccagca | ggcagaagta | tgcaaagcat | gcatctcaat | tagtcagcaa | 2040 |
| ccatagtccc | gcccctaact | ccgcccatcc | cgcccctaac | tccgcccagt | tccgcccatt | 2100 |
| ctccgcccca | tggctgacta | attttttta | tttatgcaga | ggccgaggcc | gcctctgcct | 2160 |

```
ctgagctatt ccagaagtag tgaggaggct tttttggagg cctaggcttt tgcaaaaagc   2220
tcccgggagc ttggatatcc attttcggat ctgatcaaga gacaggatga ggatcgtttc   2280
gcatgattga acaagatgga ttgcacgcag gttctccggc cgcttgggtg gagaggctat   2340
tcggctatga ctgggcacaa cagacaatcg gctgctctga tgccgccgtg ttccggctgt   2400
cagcgcaggg gcgcccggtt cttttttgtca agaccgacct gtccggtgcc ctgaatgaac   2460
tgcaggacga ggcagcgcgg ctatcgtggc tggccacgac gggcgttcct tgcgcagctg   2520
tgctcgacgt tgtcactgaa gcgggaaggg actggctgct attgggcgaa gtgccggggc   2580
aggatctcct gtcatctcac cttgctcctg ccgagaaagt atccatcatg gctgatgcaa   2640
tgcggcggct gcatacgctt gatccggcta cctgcccatt cgaccaccaa gcgaaacatc   2700
gcatcgagcg agcacgtact cggatggaag ccggtcttgt cgatcaggat gatctggacg   2760
aagagcatca ggggctcgcg ccagccgaac tgttcgccag gctcaaggcg cgcatgcccg   2820
acggcgagga tctcgtcgtg acccatggcg atgcctgctt gccgaatatc atggtggaaa   2880
atggccgctt ttctggattc atcgactgtg gccggctggg tgtggcggac cgctatcagg   2940
acatagcgtt ggctacccgt gatattgctg aagagcttgg cggcgaatgg gctgaccgct   3000
tcctcgtgct ttacggtatc gccgctcccg attcgcagcg catcgccttc tatcgccttc   3060
ttgacgagtt cttctgagcg ggactctggg gttcggtgct acgagatttc gattccaccg   3120
ccgccttcta tgaaaggttg ggcttcggaa tcgttttccg ggacgccggc tggatgatcc   3180
tccagcgcgg ggatctcatg ctggagttct tcgcccaccc caacttgttt attgcagctt   3240
ataatggtta caaataaagc aatagcatca caaatttcac aaataaagca tttttttcac   3300
tgcattctag ttgtggtttg tccaaactca tcaatgtatc ttatcatgtc tgtataccgt   3360
cgacctctag ctagagcttg gcgtaatcat ggtcatagct gtttcctgtg tgaaattgtt   3420
atccgctcac aattccacac aacatacgag ccggaagcat aaagtgtaaa gcctggggtg   3480
cctaatgagt gagctaactc acattaattg cgttgcgctc actgcccgct ttccagtcgg   3540
gaaacctgtc gtgccagctg cattaatgaa tcggccaacg cgcggggaga ggcggtttgc   3600
gtattgggcg ctcttccgct tcctcgctca ctgactcgct gcgctcggtc gttcggctgc   3660
ggcgagcggt atcagctcac tcaaaggcgg taatacggtt atccacagaa tcaggggata   3720
acgcaggaaa gaacatgtga gcaaaaggcc agcaaaaggc caggaaccgt aaaaaggccg   3780
cgttgctggc gtttttccat aggctccgcc cccctgacga gcatcacaaa aatcgacgct   3840
caagtcagag gtggcgaaac ccgacaggac tataaagata ccaggcgttt ccccctggaa   3900
gctccctcgt gcgctctcct gttccgaccc tgccgcttac cggatacctg tccgcctttc   3960
tcccttcggg aagcgtggcg ctttctcaat gctcacgctg taggtatctc agttcggtgt   4020
aggtcgttcg ctccaagctg ggctgtgtgc acgaaccccc cgttcagccc gaccgctgcg   4080
ccttatccgg taactatcgt cttgagtcca acccggtaag acacgactta tcgccactgg   4140
cagcagccac tggtaacagg attagcagag cgaggtatgt aggcggtgct acagagttct   4200
tgaagtggtg gcctaactac ggctacacta gaaggacagt atttggtatc tgcgctctgc   4260
tgaagccagt taccttcgga aaaagagttg gtagctcttg atccggcaaa caaaccaccg   4320
ctggtagcgg tggttttttt gtttgcaagc agcagattac gcgcagaaaa aaggatctc   4380 aagaagatcc tttgatcttt tctacggggt ctgacgctca gtggaacgaa aactcacgtt   4440
aagggatttt ggtcatgaga ttatcaaaaa ggatcttcac ctagatcctt ttaaattaaa   4500
aatgaagttt taaatcaatc taaagtatat atgagtaaac ttggtctgac agttaccaat   4560
```

-continued

```
gcttaatcag tgaggcacct atctcagcga tctgtctatt tcgttcatcc atagttgcct   4620
gactccccgt cgtgtagata actacgatac gggagggctt accatctggc cccagtgctg   4680
caatgatacc gcgagaccca cgctcaccgg ctccagattt atcagcaata aaccagccag   4740
ccggaagggc cgagcgcaga agtggtcctg caactttatc cgcctccatc cagtctatta   4800
attgttgccg ggaagctaga gtaagtagtt cgccagttaa tagtttgcgc aacgttgttg   4860
ccattgctac aggcatcgtg gtgtcacgct cgtcgtttgg tatggcttca ttcagctccg   4920
gttcccaacg atcaaggcga gttacatgat cccccatgtt gtgcaaaaaa gcggttagct   4980
ccttcggtcc tccgatcgtt gtcagaagta agttggccgc agtgttatca ctcatggtta   5040
tggcagcact gcataattct cttactgtca tgccatccgt aagatgcttt tctgtgactg   5100
gtgagtactc aaccaagtca ttctgagaat agtgtatgcg gcgaccgagt tgctcttgcc   5160
cggcgtcaat acgggataat accgcgccac atagcagaac tttaaaagtg ctcatcattg   5220
gaaaacgttc ttcggggcga aaactctcaa ggatcttacc gctgttgaga tccagttcga   5280
tgtaacccac tcgtgcaccc aactgatctt cagcatcttt tactttcacc agcgtttctg   5340
ggtgagcaaa aacaggaagg caaaatgccg caaaaaaggg aataagggcg acacggaaat   5400
gttgaatact catactcttc ctttttcaat attattgaag catttatcag ggttattgtc   5460
tcatgagcgg atacatattt gaatgtattt agaaaaataa acaaataggg gttccgcgca   5520
catttccccg aaaagtgcca cctgacgtc                                     5549
```

<210> SEQ ID NO 3
<211> LENGTH: 193
<212> TYPE: PRT
<213> ORGANISM: SARS-CoV

<400> SEQUENCE: 3

```
Asn Ile Thr Asn Leu Cys Pro Phe Gly Glu Val Phe Asn Ala Thr Lys
1               5                   10                  15

Phe Pro Ser Val Tyr Ala Trp Glu Arg Lys Lys Ile Ser Asn Cys Val
            20                  25                  30

Ala Asp Tyr Ser Val Leu Tyr Asn Ser Thr Phe Phe Ser Thr Phe Lys
        35                  40                  45

Cys Tyr Gly Val Ser Ala Thr Lys Leu Asn Asp Leu Cys Phe Ser Asn
    50                  55                  60

Val Tyr Ala Asp Ser Phe Val Val Lys Gly Asp Asp Val Arg Gln Ile
65                  70                  75                  80

Ala Pro Gly Gln Thr Gly Val Ile Ala Asp Tyr Asn Tyr Lys Leu Pro
                85                  90                  95

Asp Asp Phe Met Gly Cys Val Leu Ala Trp Asn Thr Arg Asn Ile Asp
            100                 105                 110

Ala Thr Ser Thr Gly Asn Tyr Asn Tyr Lys Tyr Arg Tyr Leu Arg His
        115                 120                 125

Gly Lys Leu Arg Pro Phe Glu Arg Asp Ile Ser Asn Val Pro Phe Ser
    130                 135                 140

Pro Asp Gly Lys Pro Cys Thr Pro Pro Ala Leu Asn Cys Tyr Trp Pro
145                 150                 155                 160

Leu Asn Asp Tyr Gly Phe Tyr Thr Thr Thr Gly Ile Gly Tyr Gln Pro
                165                 170                 175

Tyr Arg Val Val Val Leu Ser Phe Glu Leu Leu Asn Ala Pro Ala Thr
            180                 185                 190
```

Val

<210> SEQ ID NO 4
<211> LENGTH: 240
<212> TYPE: PRT
<213> ORGANISM: Artificial sequence
<220> FEATURE:
<223> OTHER INFORMATION: SARS-CoV S protein fragment S318-510 incuding
      additional sequences
<220> FEATURE:
<221> NAME/KEY: SIGNAL
<222> LOCATION: (1)..(21)
<223> OTHER INFORMATION:
<220> FEATURE:
<221> NAME/KEY: BINDING
<222> LOCATION: (220)..(230)
<223> OTHER INFORMATION:
<220> FEATURE:
<221> NAME/KEY: BINDING
<222> LOCATION: (235)..(240)
<223> OTHER INFORMATION:
<220> FEATURE:
<221> NAME/KEY: PEPTIDE
<222> LOCATION: (22)..(214)
<223> OTHER INFORMATION:

<400> SEQUENCE: 4

```
Met Ala Cys Pro Gly Phe Leu Trp Ala Leu Val Ile Ser Thr Cys Leu
1               5                   10                  15

Glu Phe Ser Met Ala Asn Ile Thr Asn Leu Cys Pro Phe Gly Glu Val
            20                  25                  30

Phe Asn Ala Thr Lys Phe Pro Ser Val Tyr Ala Trp Glu Arg Lys Lys
        35                  40                  45

Ile Ser Asn Cys Val Ala Asp Tyr Ser Val Leu Tyr Asn Ser Thr Phe
    50                  55                  60

Phe Ser Thr Phe Lys Cys Tyr Gly Val Ser Ala Thr Lys Leu Asn Asp
65                  70                  75                  80

Leu Cys Phe Ser Asn Val Tyr Ala Asp Ser Phe Val Val Lys Gly Asp
                85                  90                  95

Asp Val Arg Gln Ile Ala Pro Gly Gln Thr Gly Val Ile Ala Asp Tyr
            100                 105                 110

Asn Tyr Lys Leu Pro Asp Asp Phe Met Gly Cys Val Leu Ala Trp Asn
        115                 120                 125

Thr Arg Asn Ile Asp Ala Thr Ser Thr Gly Asn Tyr Asn Tyr Lys Tyr
    130                 135                 140

Arg Tyr Leu Arg His Gly Lys Leu Arg Pro Phe Glu Arg Asp Ile Ser
145                 150                 155                 160

Asn Val Pro Phe Ser Pro Asp Gly Lys Pro Cys Thr Pro Pro Ala Leu
                165                 170                 175

Asn Cys Tyr Trp Pro Leu Asn Asp Tyr Gly Phe Tyr Thr Thr Thr Gly
            180                 185                 190

Ile Gly Tyr Gln Pro Tyr Arg Val Val Val Leu Ser Phe Glu Leu Leu
        195                 200                 205

Asn Ala Pro Ala Thr Val Ser Arg Gly Pro Phe Glu Gln Lys Leu Ile
    210                 215                 220

Ser Glu Glu Asp Leu Asn Met His Thr Gly His His His His His His
225                 230                 235                 240
```

CELL LINE FOR PRODUCING CORONAVIRUSES

FIELD OF THE INVENTION

The invention relates to medicine. In particular the invention relates to the production of coronaviruses such as human SARS-CoV.

BACKGROUND OF THE INVENTION

Severe acute respiratory distress syndrome (SARS) is a new respiratory disorder in humans that is caused by the SARS coronavirus (SARS-CoV). The disease emerged at the beginning of 2003 in China and various other portions of South East Asia and has since then rapidly spread throughout the world. Although the disease had disappeared by June 2003 its re-emergence cannot be excluded. Therefore, much effort is currently being put into the development of therapeutic and prophylactic treatments for SARS-CoV.

Although SARS-CoV is phylogenetically distinct from all previously known human and animal coronaviruses, significant progress has been made in understanding the molecular and cell biology of SARS-CoV. Next to the complete sequence of the SARS-CoV genome (see Marra et al. (2003); Rota et al. (2003)), Li et al. (2003) have recently identified a zinc metallopeptidase, angiotensin-converting enzyme 2 (ACE2 protein), as a functional receptor for SARS-CoV. This and other knowledge regarding the molecular and cell biology of SARS-CoV have offered avenues for developing antiviral as well as vaccine strategies.

The development of a vaccine protecting against SARS-CoV has mainly focused on two strategies, i.e. the use of inactivated whole SARS-CoV (Tang et al. (2004); Takasuka et al. (2004)) and the use of SARS-CoV proteins (Zhang et al. (2004); Yang et al. (2004); Kim et al. (2004)). Inactivated whole virus vaccines are usually prepared by producing large amounts of virus in cell tissue culture and then rendering the virus harmless without destroying its immunological properties. For optimal virus production in cell culture, it is pivotal that the respective virus is capable of infecting the cells and replicating in the cell. To date only a limited number of cells have been reported to be susceptible to SARS-CoV infection and to support SARS-CoV replication in culture (see Mossel et al. (2005)). The most frequently used cells in that respect are kidney cells derived from African Green Monkeys such as Vero or Vero E6 cells. A disadvantage associated with these cells is inter alia that they require the presence of serum and/or the adherence to a solid support for growth resulting in purification and safety issues as well as a laborious system for large-scale production. Furthermore, the cells are not human.

Recently, it was shown that cells refractory to SARS-CoV infection could be rendered permissive for SARS-CoV replication by expressing a functional receptor, i.e. the human ACE2 receptor. In WO 2005/032487 it was shown that human 293T cells transfected with the ACE2 protein supported SARS-CoV replication and were suitable for the production of SARS-CoV. However, the yields obtained with these cells were low making production methods using them economically unattractive. Taken together, there is still a need in the art for a method of producing SARS-CoV in a host cell system that improves on the existing cell culture systems, specifically on the yields obtained.

The present invention addresses this need by providing primary human retina cells (HER cells) expressing the ACE2 protein. These cells give unexpectedly high SARS-CoV yields. They have as a further advantage that they are extensively documented and better behave in the process of upscaling, suspension growth and growth factor independence compared to the cells in the art. Especially the fact that the cells can be brought in suspension in a highly reproducible manner is something that makes them very suitable for large scale production. Moreover, the cells of the present invention can advantageously be used for the replication of various isolates of human SARS-CoV and are further not only suitable for the production of SARS-CoV, but also for production of other human coronaviruses that make use of the ACE2 protein as a functional receptor.

SUMMARY OF THE INVENTION

The invention provides cells suitable for producing coronaviruses. In a preferred embodiment the cells are HER cells expressing the human ACE2 protein. The invention further provides methods for producing coronaviruses, in particular SARS-CoV, making use of the cells.

DETAILED DESCRIPTION OF THE INVENTION

In a first aspect the present invention encompasses cells expressing the human ACE2 protein. As it has recently been found that ACE2 gene polymorphisms do not affect outcome of severe acute respiratory syndrome (see Chiu et al. (2004)), cells expressing a variant of the ACE2 protein are also part of the present invention. Said variant should of course still be capable of functioning as a receptor for SARS-CoV. The cells of the invention are E1-immortalized retina cells. They have been derived from retina cells by immortalization with adenovirus E1 sequences, e.g. E1A and E1B sequences. The E1A sequences may be under influence of their endogenous adenovirus E1A promoter, but may also be controlled by a heterologous promoter, such as for instance a PGK promoter. E1A protein has transforming activity, while E1B protein has anti-apoptotic activities. Furthermore, E1A may aid in increasing expression levels from the cells. Preferably, the cells according to the invention are derived from primary cells. They may be cells of any origin, and are preferably of human origin. In one preferred aspect, the cells are derived from primary human embryonic retina cells, in other words, the cells of the invention are derived from primary human embryonic retinoblast (HER cells) and comprise in their genome sequences that encode E1A and E1B of an adenovirus. Primary HER cells can be isolated from fetuses (see Byrd et al. (1982); Byrd et al. (1988)). Immortalization of the cells with adenoviral E1 sequences has for instance been described in U.S. Pat. No. 5,994,128. Accordingly, an embryonic retina cell that has been immortalized with E1 sequences from an adenovirus can be obtained by that method. Other cells expressing E1A and E1B of an adenovirus can be prepared accordingly.

The most preferred HER cells for the methods and uses of the invention are cells as deposited at the ECACC on 29 Feb. 1996 under number 96022940 or a derivative thereof. One E1-immortalized cell line useful for the invention, and having the characteristics of the cells deposited at the ECACC under number 96022940, is marketed under the trade mark PER.C6® by Crucell Holland B.V. PER.C6® cells for the purpose of the present application means cells from an upstream or downstream passage or a descendent of an upstream or downstream passage of cells as deposited under ECACC no. 96022940. PER.C6® behaves better in handling than for instance transformed human 293 cells that have also been immortalized by the E1 region from adenovirus. Furthermore, PER.C6® cells have been fully characterized and have been documented very extensively, while they behave significantly better in the process of upscaling, suspension growth and growth factor independence. Especially the fact that PER.C6® cells can be brought in suspension in a highly reproducible manner is something that makes them very suitable for large-scale production. Moreover, the fact that they can grow in defined serum-free medium, devoid of any human or animal serum proteins, and their growth is compatible with roller bottles, shaker flasks, spinner flasks and bioreactors, with doubling times of about 35 hrs makes them suitable as hosts for growing viruses.

The E1A and E1B sequences can be derived from any adenovirus serotype including adenovirus serotypes 2, 5, 12 and 35 (for other suitable adenovirus serotypes see for instance Table 1 in EP 1 054 064).

A cell according to the invention may comprise a polynucleotide encoding the human ACE2 protein stably integrated into the genomic material or as part of an autonomously replicating vector, i.e. the human ACE2 protein may be transiently expressed, but for long-term, high-yield expression of the human ACE2 protein stable expression is preferred. In other words, a cell according to the invention is engineered to express the human ACE2 protein. For example, the cells of the invention may be transformed using expression vectors that may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the ACE2 protein. Resistant clones of stably transformed cells may be proliferated using tissue culture techniques appropriate to the cells of the invention. A cell culture comprising a multitude of cells according to the invention is likewise part of the present invention and may be used in the methods below.

In another aspect, the invention provides a method of producing a coronavirus, e.g. a human SARS-CoV, by infecting a cell according to the invention with a coronavirus and harvesting the coronavirus from the medium or the cell. In an embodiment the production method comprises the steps of a) providing a human cell as described above, e.g. a human cell that is derived from a primary human embryonic retinoblast, said cell comprising in its genome sequences that encode E1A and E1B of an adenovirus, with a nucleic acid molecule encoding a human ACE2 protein, b) culturing the cell under conditions suitable for expression of the human ACE2 protein, c) infecting the cell with a coronavirus, and d) harvesting the coronavirus from the medium or the cell. The cells are cultured for optimal expression of the ACE2 protein. This may be achieved in conventional media of the cells. If necessary, the media may be modified e.g. for appropriate selection, amplification or induction of transcription. The culture conditions for the cells such as temperature, pH, nutrients etc. are well known to those ordinary skilled in the art. The engineered cells are cultured under conditions conducive to the production of the coronavirus. Harvesting may start as soon as CPE is observed. The produced coronavirus can be recovered/harvested from the cell free extract, but also from the culture medium. Methods to recover viruses from cell free extracts or culture medium are well known to the man skilled in the art and may include centrifugation or chromatographic steps. Preferably, the human cell used in the method is PER.C6® as deposited under ECACC no. 96022940 or a derivative thereof. In a preferred embodiment the human cell is capable of growing in suspension and/or can be cultured in the absence of serum.

In a preferred embodiment the coronavirus is selected from the group consisting of coronaviruses using the ACE2 protein as a receptor for infectious entry. Such coronaviruses include, but are not limited to, human coronaviruses including human SARS-CoV isolates and human CoV-NL63 (see Hofmann et al. (2005)). In an embodiment the engineered cells may be suitable for producing all human SARS-CoV isolates (for a list of known human SARS-CoV isolates see Table 1).

The human ACE2 protein can be transiently expressed but is preferably stably expressed. The nucleic acid molecule encoding the human ACE2 protein can be provided to the cell by a suitable nucleic acid construct, e.g. a vector. Vectors can be derived from plasmids such as inter alia F, R1, RP1, Col, pBR322, TOL, Ti, etc; cosmids; phages such as lambda, lambdoid, M13, Mu, P1, P22, Qβ, T-even, T-odd, T2, T4, T7, etc; plant viruses; or animal viruses. The choice of the vector is dependent on the recombinant procedures followed and the cells used. Introduction of vectors in host cells can be effected by inter alia calcium phosphate transfection, virus infection, DEAE-dextran mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical to the invention as is well known to persons skilled in the art. They include, but are not limited to, kanamycin, neomycin, puromycin, hygromycin, zeocin, thymidine kinase gene from Herpes simplex virus (HSV-TK), dihydrofolate reductase gene from mouse (dhfr). If necessary, vectors may comprising a nucleic acid molecule encoding the ACE2 protein operably linked to one or more nucleic acid molecules encoding proteins or peptides that can be used for isolation purposes. These proteins or peptides include, but are not limited to, glutathione-S-transferase, maltose binding protein, metal-binding polyhistidine, green fluorescent protein, luciferase and beta-galactosidase. The nucleic acid construct may comprise an expression-regulating nucleic acid sequence. This term as used herein refers to polynucleotide sequences necessary for and/or affecting the expression of an operably linked coding sequence in a particular host organism. The expression-regulating nucleic acid sequences, such as inter alia appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g. ribosome binding sites); sequences that enhance protein stability; and when desired, sequences that enhance protein secretion, can be any nucleic acid sequence showing activity in the host organism of choice and can be derived from genes encoding proteins, which are either homologous or heterologous to the host organism. The identification and employment of expression-regulating sequences is routine to the person skilled in the art. Expression and/or transfection vectors frequently used include plasmid vectors and retroviruses. Plasmid vectors are preferred in the present invention as retroviruses have the disadvantage that they infect and integrate only dividing cells. Other problems include cumbersome preparation and relatively low titer, size constraints on inserted genes, difficulties in controlling or ensuring expression, and the potential for genetic damage due to random integration in the host genome. Safety issues that arise from the use of retroviruses in the laboratory involving potential toxicities, particularly from viruses that can infect human cells, are a further disadvantage of the use of retroviruses.

In another aspect the invention provides a method further comprising the step of inactivating or attenuating the harvested coronavirus. The inactivated or attenuated coronavirus may be purified before, during or after the inactivation or attenuation step. Purification may be performed by means of purification methods suitable for viruses such as for instance centrifugation through a glycerol cushion and other methods well known to a person of ordinary skill in the art. Inactivation may be performed by methods well known to the skilled artisan such as gamma- or UV irradiation, heat treatment or treatment with chemicals such as formaldehyde, acetone, alcohol and alkylating agents like ethylene oxide, ethyleneimine, acetylehtyleneimine and B-propiolactone. Following the inactivation step the viruses may be tested for the absence of infectivity in cell culture. Methods to test if a virus is still infective or partly or completely inactivated are also well known to the person skilled in the art. Once absence of infectivity is established, the thus obtained inactivated virus preparation can be used for further purposes e.g. vaccine preparation.

Attenuation reduces the virulence of the virus so that, although it is still alive, it can no longer cause disease. The most common method of attenuation involves adapting organisms to growth in unusual conditions so that they lose their adaptation to their usual host. The most commonly used method of virus attenuation is prolonged tissue culture growth. Prolonged tissue culture growth involves infecting tissue culture plates with the virus for many generations. Due to the virus not having to be virulent in tissue culture there is no selection for virulence and the virus loses its ability to cause disease. The tissue culture that is used for production of attenuated vaccines is preferably from the same species that will be vaccinated with the attenuated vaccine in order to decrease the chance of immune reaction to the tissue. In that respect human cells are preferred as tissue culture system.

The inactivated or attenuated coronaviruses may be used in vaccines. Vaccines may be formulated by means known in the art. Usually this may involve the addition of an adjuvant and/or a suitable carrier.

In an embodiment the virus titer of the coronavirus harvested is at least 4.00, 4.25, 4.50, 4.75, 5.00, 5.25, 5.50, 5.75, 6.00, 6.25, 6.50, 6.75, 7.00, 7.25, 7.50, and preferably at least 7.75 log10 $TCID_{50}$/ml after 24 hours post infection.

Furthermore, the present invention provides the use of a human cell according to the invention for the production of a coronavirus, preferably a human coronavirus such as human SARS-CoV or HCoV-NL63. The human cell according to the invention can also be used for the screening of antiviral agents against a coronavirus. The antiviral agents can be molecules or compounds that affect the binding of the virus to the receptor or affect the receptor function of the ACE2 protein in any other way. They can for instance be obtained by measuring the binding of a candidate molecule to the cells or membranes of the cells bearing the ACE2 protein and may include chemical compounds, peptides, polypeptides, antibodies or fragments thereof In yet another aspect, the invention provides a method for identifying a molecule capable of inhibiting coronavirus infection and/or replication, the method comprising the steps of a) incubating a cell according to the invention with a coronavirus in the presence and absence of the candidate molecule, and b) determining whether the presence of the candidate molecule inhibits coronavirus infection and/or replication. A person skilled in the art is aware that several steps of the methods of the invention including washing steps and incubation conditions need optimization. The virus and the candidate molecule may be mixed together before being contacted with the cells. The invention also provides a method for selecting an antiviral molecule that is capable of reducing infection of a cell by a coronavirus, wherein the method comprises the steps of a) contacting a cell according to the invention with a surface protein of a coronavirus in the presence or absence of a candidate antiviral molecule, said surface protein being involved in binding of the coronavirus to the human ACE2 protein expressed by the cell, such as a coronavirus S protein, b) measuring the binding interaction between the cell and the surface protein, and c) selecting a candidate antiviral molecule whereby the binding interaction in the presence of the candidate antiviral molecule is reduced or decreased when compared to the binding interaction in the absence of the candidate antiviral molecule. Membranes bearing the ACE2 protein may also be used in the above selection method. The cells and membranes may also be used in a screening assay used in screening compound libraries for compounds that specifically bind to the ACE2 protein. Since the ACE2 protein plays a role in entrance of certain coronaviruses, such human SARS-CoV and HcoV-NL63, into cells, such compounds may be used in treating or preventing coronavirus infections. Thus, the present invention provides for a method for screening compounds, which affect this function of the human ACE2 protein. These compounds may inhibit the function of the receptor. Compounds and molecules that may be identified with the screening/identification/selection method of the invention may be derived from a variety of sources including chemical compound libraries or mixtures of (natural) compounds. The methods may involve measuring the binding of a candidate molecule or compound to the cells of the present invention or membranes thereof bearing the ACE2 protein. Binding may be measured directly or indirectly. Binding may be measured directly, for example, by means of label associated with the candidate molecule. Binding may also be measured indirectly. For example, indirectly measuring the binding of a candidate molecule may involve competition with a (labeled) competitor. The measuring of binding of a candidate molecule may, for example, also be determined in a cell-based assay, wherein it can be determined whether a candidate molecule is able to block the coronavirus from entering a cell. In that case it can be determined whether, in the presence of the candidate molecule or compound, cells can still be infected with the coronavirus. Alternatively, labeled human SARS-CoV S protein or a fragment responsible for binding to ACE2 protein can be contacted with cells of the invention in the presence or absence of candidate compounds. Next, it can be determined if the candidate compounds decrease the amount of S protein or fragment bound to the cells. Candidate molecules or compounds can be chemical compounds or can likewise be other molecules, e.g. antibodies or antibody fragments. The candidate molecule or compound may be capable of binding to the ACE2 protein or may be capable of binding to a protein of the coronavirus involved in infection and/or replication such as the S protein. Alternatively, the candidate molecule or compound may in any other way decrease or inhibit/abolish virus entry and/or replication. The candidate molecules or compounds that do inhibit coronavirus infection and/or replication can be used in methods of treating or preventing coronavirus infection.

EXAMPLES

To illustrate the invention, the following examples are provided. The examples are not intended to limit the scope of the invention in any way.

Example 1

Generation of A Stably Transfected Human ACE2 PER.C6® Cell Line

To evaluate the ability to grow SARS-CoV and other coronaviruses on PER.C6® cells that recombinantly express angiotensin-converting enzyme 2 (ACE2), a natural receptor for inter alia human SARS-CoV and HCoV-NL63, PER.C6® cells were transfected with a plasmid carrying the cDNA sequence encoding the ACE2 protein (see Donoghue et al. (2000) and Tipnis et al. (2000); see also GenBank numbers AAF78220 and AAF99721; and SEQ ID NO:1). Stable transfectants were selected using standard techniques known to a person skilled in the art (see Coligan J E, Dunn B M, Ploegh H L, Speicher D W and Wingfield P T (eds.) (2001) Current protocols in protein science, volume I. John Wiley & Sons, Inc., New York). The cDNA encoding the ACE2 protein was cloned as a HindIII-XbaI fragment in pcDNA2004neo(-) (SEQ ID NO:2). DNA transfections in PER.C6® cells were performed using standard techniques. Stable clones were selected in the presence of 0.5 mg/ml G418 (Gibco). Expression of ACE2 was monitored using flow cytometry. Transfected cells were incubated with goat anti-human ACE2 ectodomain polyclonal antibodies (R&D systems) for one hour at 4° C. Cells were washed three times with PBS containing 0.5% BSA, incubated for 45 minutes with phycoerythrin-conjugated F(ab')2 donkey anti-goat IgG, and analyzed on a FACSCalibur using CELLQuest Pro software (Becton Dickinson). Analysis revealed that approximately 40% of the assayed clones expressed ACE2 protein. All clones expressing ACE2 protein bound the SARS-CoV S318-510 fragment (see Example 3 below).

Example 2

Production of Human SARS-CoV On ACE2 Protein Expressing PER.C6® Cells

To evaluate whether stably ACE2-transfected PER.C6® cells were permissive for human SARS-CoV and supported the growth of human SARS-CoV, three sets of ACE2 protein expressing PER.C6® cell cultures were infected in parallel with human SARS-CoV Frankfurt 1 strain at a multiplicity of infection (MOI) of 0.1. SARS-CoV permissive Vero cells were included as a positive control cell line. Supernatants of the infected cultures were harvested and snap-frozen at −80° C. after 12, 24, 48 and 72 hours post infection (pi). After collection of all samples, the supernatants were thawed and cleared by centrifugation. Serial 10-fold dilutions were made and titrated on a confluent culture of Vero cells to determine the titer. The calculated titers indicated in Table 2 show that PER.C6® cells expressing human ACE2 protein are capable of producing SARS-CoV to levels similar as those observed for Vero cells and higher than those observed for other cells such as 293T cells engineered to express the ACE2 protein.

Example 3

Binding of Spike Protein Fragments To ACE2 Protein Expressing PER.C6® Cells Flow cytometry analysis was used to assay binding of recombinant fragments of the S protein to ACE2 transfected PER.C6® cells. PER.C6® cells expressing ACE2 were incubated for 1 hour at 4° C. with saturating concentrations of myc-tagged S318-510 fragments. Construction and expression of recombinant S fragments was performed essentially as described in van den Brink et al. (2005). Briefly, amino acids 318-510 of the S1 subunit of the spike glycoprotein of SARS-CoV strain Frankfurt 1 were transiently expressed as myc/His-tagged proteins in 293T cells and purified using Ni-chromatography (for amino acid sequence of wild-type Frankfurt 1 S318-510 fragment see SEQ ID NO:3; for amino acid sequence of S318-510 fragment including signal sequence, myc tag and his tag see SEQ ID NO:4).

Figure 1:
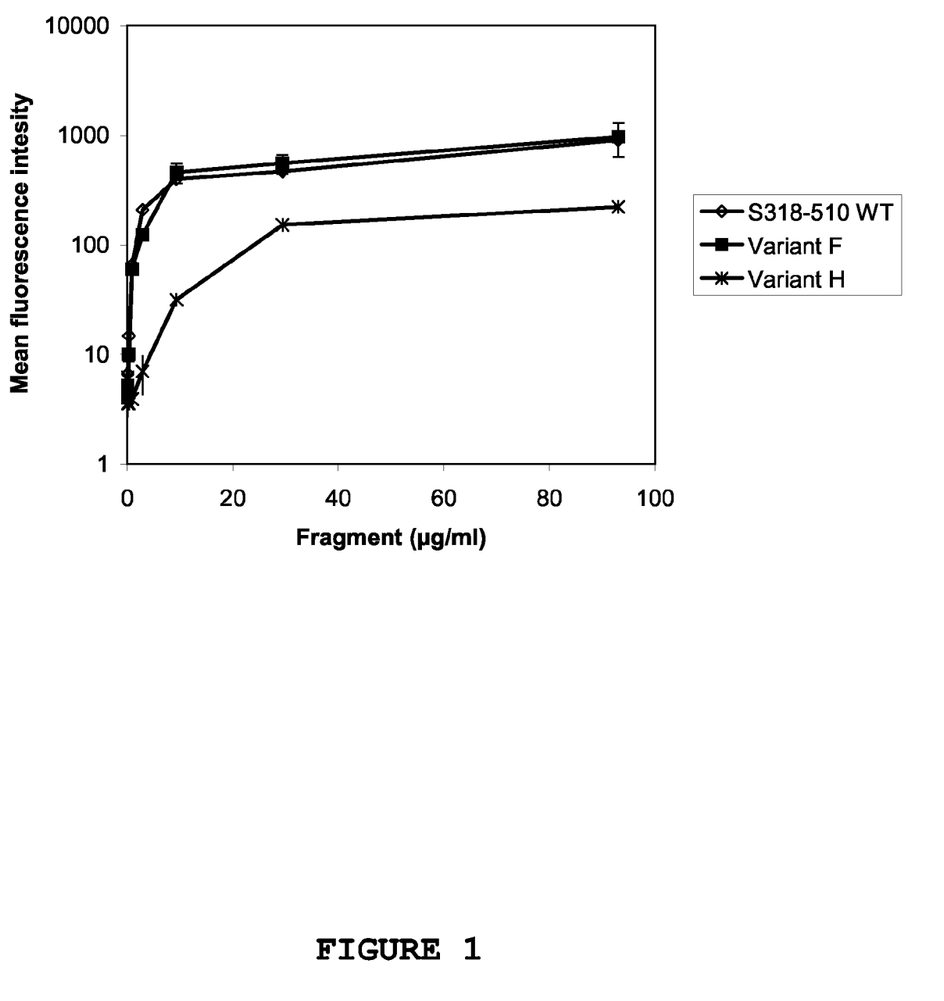
FIG. 1 shows binding of SARS-CoV S protein fragments (amino acids 318 to 510) to PER.C6® cells expressing ACE2 protein. Variant F comprises mutation N479S and variant H comprises mutations K344R, F360S, L472P, D480G, T487S compared to wild-type S318-510 fragment.

Next, selected mutations derived from published human SARS-CoV S protein sequences were introduced in the S318-510 fragment. The mutations correspond to mutations found in strains BJ302 cl.2 (variant F; GenBank no. AY429073; mutation N479S) and GD03T0013 (variant H; GenBank no. AY525636; mutations K344R, F360S, L472P, D480G, T487S). After three washes, bound fragment were detected by flow cytometry analysis by using biotinylated anti-myc antibody (Santa Cruz Biotechnology Inc.) and streptavidin-conjugated phycoerythrin (Caltag). All incubations and washes were performed at 4° C. in PBS, supplemented with 0.5% bovine serum albumin (BSA). Binding of the anti-ACE2 IgG and the recombinant S fragment revealed that no loss in ACE2 expression was observed after 18 passage numbers (data not shown). As shown in FIG. 1, all fragments were capable of binding to the PER.C6® cells expressing ACE2 protein, with the strongest binding detected for wild-type S318-510 fragment and fragment variant F. The binding of S protein fragments of several human SARS-CoV isolates to PER.C6® cells expressing ACE2 protein shows that the cells can be used to produce human SARS-CoV isolates in general.

TABLE 1

List of human SARS-CoV isolates that can be grown on ACE2 protein expressing PER.C6 ® cells.

| Virus isolate | Gene/genome | Genbank | FASTA |
|---|---|---|---|
| SARS coronavirus AS | SARS coronavirus AS, complete genome. | AY427439 | 37576845 |
| SARS coronavirus BJ01 | SARS coronavirus BJ01, complete genome. | AY278488 | 30275666 |
| SARS coronavirus BJ02 | SARS coronavirus BJ02, complete genome. | AY278487 | 31416292 |
| SARS coronavirus BJ03 | SARS coronavirus BJ03, complete genome. | AY278490 | 31416305 |

TABLE 1-continued

List of human SARS-CoV isolates that can be grown
on ACE2 protein expressing PER.C6 ® cells.

| Virus isolate | Gene/genome | Genbank | FASTA |
|---|---|---|---|
| SARS coronavirus BJ04 | SARS coronavirus BJ04, complete genome. | AY279354 | 31416306 |
| SARS coronavirus BJ2232 | | | |
| SARS coronavirus BJ302 | | | |
| SARS coronavirus CUHK-AG01 | SARS coronavirus CUHK-AG01, complete genome. | AY345986 | 33114190 |
| SARS coronavirus CUHK-AG02 | SARS coronavirus CUHK-AG02, complete genome. | AY345987 | 33114202 |
| SARS coronavirus CUHK-AG03 | SARS coronavirus CUHK-AG03, complete genome. | AY345988 | 33114214 |
| SARS coronavirus CUHK-L2 | | | |
| SARS coronavirus CUHK-Su10 | SARS coronavirus CUHK-Su10, complete genome. | AY282752 | 38304867 |
| SARS coronavirus CUHK-W1 | SARS coronavirus CUHK-W1, complete genome. | AY278554 | 30027610 |
| SARS coronavirus cw037 | | | |
| SARS coronavirus cw049 | | | |
| SARS coronavirus FRA | SARS coronavirus FRA, complete genome. | AY310120 | 33578015 |
| SARS coronavirus Frankfurt 1 | SARS coronavirus Frankfurt 1, complete genome. | AY291315 | 31581502 |
| SARS coronavirus GD01 | SARS coronavirus GD01, complete genome. | AY278489 | 31416290 |
| SARS coronavirus GD03T0013 | SARS coronavirus GD03T0013 spike glycoprotein gene, complete cds. | AY525636 | 41764105 |
| SARS coronavirus GD69 | SARS coronavirus GD69, complete genome. | AY313906 | 37960831 |
| SARS coronavirus GZ-A | SARS coronavirus GZ-A, partial genome. | AY394977 | 37624320 |
| SARS coronavirus GZ-B | SARS coronavirus GZ-B, complete genome. | AY394978 | 37624321 |
| SARS coronavirus GZ-C | SARS coronavirus GZ-C, complete genome. | AY394979 | 37624322 |
| SARS coronavirus GZ-D | SARS coronavirus GZ-D, partial genome. | AY394980 | 37624323 |
| SARS coronavirus GZ02 | SARS coronavirus GZ02, complete genome. | AY390556 | 41323719 |
| SARS coronavirus GZ43 | SARS coronavirus GZ43, partial genome. | AY304490 | 34482141 |
| SARS coronavirus GZ50 | SARS coronavirus GZ50, complete genome. | AY304495 | 34482146 |
| SARS coronavirus GZ60 | SARS coronavirus GZ60, partial genome. | AY304491 | 34482142 |
| SARS coronavirus HB | | | |
| SARS coronavirus HGZ8L1-A | SARS coronavirus HGZ8L1-A, partial genome. | AY394981 | 37624324 |
| SARS coronavirus HGZ8L1-B | SARS coronavirus HGZ8L1-B, partial genome. | AY394982 | 37624325 |
| SARS coronavirus HGZ8L2 | SARS coronavirus HGZ8L2, complete genome. | AY394993 | 37624336 |
| SARS coronavirus HKU-36871 | SARS coronavirus HKU-36871, partial genome. | AY304492 | 34482143 |
| SARS coronavirus HKU-39849 | SARS coronavirus HKU-39849, complete genome. | AY278491 | 30023963 |
| SARS coronavirus HKU-65806 | SARS coronavirus HKU-65806, partial genome. | AY304493 | 34482144 |
| SARS coronavirus HKU-66078 | SARS coronavirus HKU-66078, partial genome. | AY304494 | 34482145 |
| SARS coronavirus Hong Kong/03/2003 | | | |
| SARS coronavirus HPZ-2003 | | | |
| SARS coronavirus HSR 1 | SARS coronavirus HSR 1, complete genome. | AY323977 | 33115118 |
| SARS coronavirus HSZ-A | SARS coronavirus HSZ-A, partial genome. | AY394984 | 37624327 |
| SARS coronavirus HSZ-Bb | SARS coronavirus HSZ-Bb, complete genome. | AY394985 | 37624328 |
| SARS coronavirus HSZ-Bc | SARS coronavirus HSZ-Bc, complete genome. | AY394994 | 37624337 |
| SARS coronavirus HSZ-Cb | SARS coronavirus HSZ-Cb, complete genome. | AY394986 | 37624329 |
| SARS coronavirus HSZ-Cc | SARS coronavirus HSZ-Cc, complete genome. | AY394995 | 37624338 |

TABLE 1-continued

List of human SARS-CoV isolates that can be grown
on ACE2 protein expressing PER.C6 ® cells.

| Virus isolate | Gene/genome | Genbank | FASTA |
|---|---|---|---|
| SARS coronavirus HSZ2-A | SARS coronavirus HSZ2-A, complete genome. | AY394983 | 37624326 |
| SARS coronavirus HZS2-Bb | SARS coronavirus HZS2-Bb, partial genome. | AY395004 | 37624347 |
| SARS coronavirus HZS2-C | SARS coronavirus HZS2-C, complete genome. | AY394992 | 37624335 |
| SARS coronavirus HZS2-D | SARS coronavirus HZS2-D, complete genome. | AY394989 | 37624332 |
| SARS coronavirus HZS2-E | SARS coronavirus HZS2-E, complete genome. | AY394990 | 37624333 |
| SARS coronavirus HZS2-Fb | SARS coronavirus HZS2-Fb, complete genome. | AY394987 | 37624330 |
| SARS coronavirus HZS2-Fc | SARS coronavirus HZS2-Fc, complete genome. | AY394991 | 37624334 |
| SARS coronavirus JMD | SARS coronavirus JMD, partial genome. | AY394988 | 37624331 |
| SARS coronavirus LC1 | SARS coronavirus LC1, complete genome. | AY394998 | 37624341 |
| SARS coronavirus LC2 | SARS coronavirus LC2, complete genome. | AY394999 | 37624342 |
| SARS coronavirus LC3 | SARS coronavirus LC3, complete genome. | AY395000 | 37624343 |
| SARS coronavirus LC4 | SARS coronavirus LC4, complete genome. | AY395001 | 37624344 |
| SARS coronavirus LC5 | SARS coronavirus LC5, complete genome. | AY395002 | 37624345 |
| SARS coronavirus NS-1 | SARS coronavirus NS-1, complete genome. | AY508724 | 40795744 |
| SARS coronavirus PUMC01 | SARS coronavirus PUMC01, complete genome. | AY350750 | 38231927 |
| SARS coronavirus PUMC02 | SARS coronavirus PUMC02, complete genome. | AY357075 | 38231932 |
| SARS coronavirus PUMC03 | SARS coronavirus PUMC03, complete genome. | AY357076 | 38231937 |
| SARS coronavirus sf098 | | | |
| SARS coronavirus sf099 | | | |
| SARS coronavirus ShanghaiQXC1 | SARS coronavirus ShanghaiQXC1, complete genome. | AY463059 | 40457433 |
| SARS coronavirus ShanghaiQXC2 | SARS coronavirus ShanghaiQXC2, complete genome. | AY463060 | 40457448 |
| SARS coronavirus Shanhgai LY | SARS coronavirus Shanhgai LY spike glycoprotein gene, complete cds. | AY322205S3 | 32454341 |
| SARS coronavirus Sin0409 | | | |
| SARS coronavirus Sin2500 | SARS coronavirus Sin2500, complete genome. | AY283794 | 30468042 |
| SARS coronavirus Sin2677 | SARS coronavirus Sin2677, complete genome. | AY283795 | 30468043 |
| SARS coronavirus Sin2679 | SARS coronavirus Sin2679, complete genome. | AY283796 | 30468044 |
| SARS coronavirus Sin2748 | SARS coronavirus Sin2748, complete genome. | AY283797 | 30468045 |
| SARS coronavirus Sin2774 | SARS coronavirus Sin2774, complete genome. | AY283798 | 37361915 |
| SARS coronavirus Sin3408 | SARS coronavirus Sin3408, complete genome | AY559083 | 45644998 |
| SARS coronavirus Sin3408L | SARS coronavirus Sin3408L, complete genome | AY559097 | 45645024 |
| SARS coronavirus Sin3725V | SARS coronavirus Sin3725V, complete genome | AY559087 | 45645004 |
| SARS coronavirus Sin3765V | SARS coronavirus Sin3765V, complete genome | AY559084 | 45645000 |
| SARS coronavirus Sin842 | SARS coronavirus Sin842, complete genome | AY559081 | 45644994 |
| SARS coronavirus Sin845 | SARS coronavirus Sin845, complete genome | AY559093 | 45645019 |
| SARS coronavirus Sin846 | SARS coronavirus Sin846, complete genome | AY559094 | 45645021 |
| SARS coronavirus Sin847 | SARS coronavirus Sin847, complete genome | AY559095 | 45645022 |
| SARS coronavirus Sin848 | SARS coronavirus Sin848, complete genome | AY559085 | 45645001 |
| SARS coronavirus Sin849 | SARS coronavirus Sin849, complete genome | AY559086 | 45645003 |

TABLE 1-continued

List of human SARS-CoV isolates that can be grown on ACE2 protein expressing PER.C6 ® cells.

| Virus isolate | Gene/genome | Genbank | FASTA |
|---|---|---|---|
| SARS coronavirus Sin850 | SARS coronavirus Sin850, complete genome | AY559096 | 45645023 |
| SARS coronavirus Sin852 | SARS coronavirus Sin852, complete genome | AY559082 | 45644996 |
| SARS coronavirus Sin_WNV | | | |
| SARS coronavirus Sino1-11 | SARS coronavirus Sino1-11, complete genome. | AY485277 | 38505482 |
| SARS coronavirus Sino3-11 | SARS coronavirus Sino3-11, complete genome. | AY485278 | 38505491 |
| SARS coronavirus SinP1 | SARS coronavirus SinP1, complete genome | AY559088 | 45645007 |
| SARS coronavirus SinP2 | SARS coronavirus SinP2, complete genome | AY559089 | 45645010 |
| SARS coronavirus SinP3 | SARS coronavirus SinP3, complete genome | AY559090 | 45645013 |
| SARS coronavirus SinP4 | SARS coronavirus SinP4, complete genome | AY559091 | 45645016 |
| SARS coronavirus SinP5 | SARS coronavirus SinP5, complete genome | AY559092 | 45645017 |
| SARS coronavirus SoD | SARS coronavirus SoD, complete genome. | AY461660 | 38385714 |
| SARS coronavirus SZ1 | SARS coronavirus SZ1, partial genome. | AY304489 | 34482140 |
| SARS coronavirus SZ13 | SARS coronavirus SZ13, partial genome. | AY304487 | 34482138 |
| SARS coronavirus SZ16 | SARS coronavirus SZ16, complete genome. | AY304488 | 34482139 |
| SARS coronavirus SZ3 | SARS coronavirus SZ3, complete genome. | AY304486 | 34482137 |
| SARS coronavirus Taiwan | | | |
| SARS coronavirus Taiwan JC-2003 | | | |
| SARS coronavirus Taiwan TC1 | SARS coronavirus Taiwan TC1, complete genome. | AY338174 | 32493129 |
| SARS coronavirus Taiwan TC2 | SARS coronavirus Taiwan TC2, complete genome. | AY338175 | 32493130 |
| SARS coronavirus Taiwan TC3 | SARS coronavirus Taiwan TC3, complete genome. | AY348314 | 33188324 |
| SARS coronavirus Tor2 | SARS coronavirus TOR2, complete genome. | AY274119 | 30248028 |
| SARS coronavirus TW | | | |
| SARS coronavirus TW-GD1 | | | |
| SARS coronavirus TW-GD2 | | | |
| SARS coronavirus TW-GD3 | | | |
| SARS coronavirus TW-GD4 | | | |
| SARS coronavirus TW-GD5 | | | |
| SARS coronavirus TW-HP1 | | | |
| SARS coronavirus TW-HP2 | | | |
| SARS coronavirus TW-HP3 | | | |
| SARS coronavirus TW-HP4 | | | |
| SARS coronavirus TW-JC2 | | | |
| SARS coronavirus TW-KC1 | | | |
| SARS coronavirus TW-KC3 | | | |
| SARS coronavirus TW-PH1 | | | |
| SARS coronavirus TW-PH2 | | | |
| SARS coronavirus TW-YM1 | | | |
| SARS coronavirus TW-YM2 | | | |
| SARS coronavirus TW-YM3 | | | |
| SARS coronavirus TW-YM4 | | | |
| SARS coronavirus TW1 | SARS coronavirus TW1, complete genome. | AY291451 | 30698326 |
| SARS coronavirus TW10 | SARS coronavirus TW10, complete genome. | AY502923 | 40548873 |
| SARS coronavirus TW11 | SARS coronavirus TW11, complete genome. | AY502924 | 40548885 |
| SARS coronavirus TW2 | SARS coronavirus TW2, complete genome. | AY502925 | 40548897 |
| SARS coronavirus TW3 | SARS coronavirus TW3, complete genome. | AY502926 | 40548909 |
| SARS coronavirus TW4 | SARS coronavirus TW4, complete genome. | AY502927 | 40548921 |
| SARS coronavirus TW5 | SARS coronavirus TW5, complete genome. | AY502928 | 40548933 |

TABLE 1-continued

List of human SARS-CoV isolates that can be grown
on ACE2 protein expressing PER.C6 ® cells.

| Virus isolate | Gene/genome | Genbank | FASTA |
| --- | --- | --- | --- |
| SARS coronavirus TW6 | SARS coronavirus TW6, complete genome. | AY502929 | 40548945 |
| SARS coronavirus TW7 | SARS coronavirus TW7, complete genome. | AY502930 | 40548957 |
| SARS coronavirus TW8 | SARS coronavirus TW8, complete genome. | AY502931 | 40548969 |
| SARS coronavirus TW9 | SARS coronavirus TW9, complete genome. | AY502932 | 40548981 |
| SARS coronavirus TWC | SARS coronavirus TWC, complete genome. | AY321118 | 31873092 |
| SARS coronavirus TWC2 | SARS coronavirus TWC2, complete genome. | AY362698 | 33518724 |
| SARS coronavirus TWC3 | SARS coronavirus TWC3, complete genome. | AY362699 | 33518725 |
| SARS coronavirus TWH | SARS coronavirus TWH genomic RNA, complete genome. | AP006557 | 33411399 |
| SARS coronavirus TWJ | SARS coronavirus TWJ genomic RNA, complete genome. | AP006558 | 33411414 |
| SARS coronavirus TWK | SARS coronavirus TWK genomic RNA, complete genome. | AP006559 | 33411429 |
| SARS coronavirus TWS | SARS coronavirus TWS genomic RNA, complete genome. | AP006560 | 33411444 |
| SARS coronavirus TWY | SARS coronavirus TWY genomic RNA, complete genome. | AP006561 | 33411459 |
| SARS coronavirus Urbani | SARS coronavirus Urbani, complete genome. | AY278741 | 30027617 |
| SARS coronavirus Vietnam | | | |
| SARS coronavirus WHU | SARS coronavirus WHU, complete genome. | AY394850 | 40795428 |
| SARS coronavirus xw002 | | | |
| SARS coronavirus ZJ01 | SARS coronavirus ZJ01, complete genome. | AY297028 | 30910859 |
| SARS coronavirus ZMY 1 | SARS coronavirus ZMY 1, complete genome. | AY351680 | 33304219 |
| SARS coronavirus ZS-A | SARS coronavirus ZS-A, complete genome. | AY394997 | 37624340 |
| SARS coronavirus ZS-B | SARS coronavirus ZS-B, complete genome. | AY394996 | 37624339 |
| SARS coronavirus ZS-C | SARS coronavirus ZS-C, complete genome. | AY395003 | 37624346 |
| | SARS coronavirus, TOR2 complete genome, curated | NC_004718 | 30271926 |
| | SARS coronavirus ZJ01, partial genome. | AY286320 | 39980888 |
| | SARS coronavirus BJ302 clone 1 spike glycoprotein gene, complete | AY429072 | 38016580 |
| | SARS coronavirus BJ302 clone 2 spike glycoprotein gene, complete | AY429073 | 38016582 |
| | SARS coronavirus BJ302 clone 3 spike glycoprotein gene, complete | AY429074 | 38016584 |
| | SARS coronavirus BJ302 clone 4 spike glycoprotein gene, complete | AY429075 | 38016586 |
| | SARS coronavirus BJ302 clone 5 spike glycoprotein gene, complete | AY429076 | 38016588 |
| | SARS coronavirus BJ302 clone 6 spike glycoprotein gene, complete | AY429077 | 38016590 |
| | SARS coronavirus BJ302 clone 7 spike glycoprotein gene, complete | AY429078 | 38016592 |
| | SARS coronavirus BJ302 clone 8 spike glycoprotein gene, complete | AY429079 | 38016594 |
| Human coronavirus NL63 | Human Coronavirus NL63, complete genome | AY567487 | 49035964 |
| Human group 1 coronavirus associated with pneumonia | Human group 1 coronavirus associated with pneumonia, complete genome | AY518894 | 46369870 |

TABLE 2

SARS-CoV titers measured in culture supernatants harvested after 12, 24, 48 and 72 hours post-infection of PER.C6 ® and Vero cultures at MOI 0.1. Titers were expressed in log10 ± log10 standard error.

| hr pi | PER.C6 ®-ACE2 | | | Vero | | |
|---|---|---|---|---|---|---|
| 12 | 5.05 ± 0.16 | 5.05 ± 0.16 | 5.30 ± 0.19 | 7.30 ± 0.23 | 7.05 ± 0.16 | 7.05 ± 0.16 |
| 24 | 7.93 ± 0.13 | 7.55 ± 0.25 | 6.93 ± 0.13 | 7.43 ± 0.18 | 7.18 ± 0.21 | 7.05 ± 0.16 |
| 48 | 6.05 ± 0.16 | 6.18 ± 0.18 | 6.43 ± 0.18 | 7.05 ± 0.18 | 6.80 | 7.43 ± 0.18 |
| 72 | 6.80 ± 0.29 | 6.18 ± 0.30 | 5.93 ± 0.21 | 6.80 ± 0.18 | 6.55 ± 0.16 | 6.68 ± 0.13 |

REFERENCES

Byrd P, Brown K W, and Gallimore P H. 1982. Malignant transformation of human embryo retinoblasts by cloned adenovirus 12 DNA. Nature 298:69-71.

Byrd P J, Grand R J A, and Gallimore P H. 1988. Differential transformation of primary human embryo retinal cells by adenovirus E1 regions and combinations of E1A+ras. Oncogene 2:477-484.

Chiu R W, Tang N L, Hui D S, Chung G T, Chim S S, Chan K C, Sung Y M, Chan L Y, Tong Y K, Lee W S, Chan P K, and Lo Y M (2004). ACE2 gene polymorphisms do not affect outcome of severe acute respiratory syndrome. Clin. Chem. 50:1683-1686.

Donoghue M, Hsieh F, Baronas E, Godbout K, Gosselin M, Stagliano N, Donovan M, Woolf B, Robison K, Jeyaseelan R, Breitbart R E, and Acton S. 2000. A novel angiotensin-converting enzyme-related carboxypeptidase (ACE2) converts angiotensin I to angiotensin 1-9. Circ. Res. 87:E1-9.

Hofmann H, Pyrc K, van der Hoek L, Geier M, Berkhout B, and Pohlmann S. 2005. Human coronavirus NL63 employs the severe acute respiratory syndrome coronavirus receptor for cellular entry. Proc. Natl. Acad. Sci. U.S.A. 102:7988-7993.

Kim T W, Lee J H, Hung C F, Peng S, Roden R, Wang M C, Viscidi R, Tsai Y C, He L, Chen P J, Boyd D A, and Wu T C. 2004. Generation and characterization of DNA vaccines targeting the nucleocapsid protein of severe acute respiratory syndrome coronavirus. J. Virol. 78:4638-4645.

Li W, Moore M J, Vasilieva N, Sui J, Wong S K, Berne M A, Somasundaran M, Sullivan J L, Luzuriaga K, Greenough T C, Choe H, and Farzan M. 2003. Angiotensin-converting enzyme 2 is a functional receptor for the SARS coronavirus. Nature 426:450-454.

Marra M A, et al. 2003. The genome sequence of the SARS-associated coronavirus. Science 300:1399-1404.

Mossel E C, Huang C, Narayanan K, Makino S, Tesh R B, and Peters C J. 2005. Exogenous ACE2 expression allows refractory cell lines to support severe acute respiratory syndrome coronavirus replication. J. Virol. 79:3846-3850.

Rota P A, et al. 2003. Characterization of a novel coronavirus associated with severe acute respiratory syndrome. Science 300:1394-1399.

Takasuka N, Fujii H, Takahashi Y, Kasai M, Morikawa S, Itamura S, Ishii K, Sakaguchi M, Ohnishi K, Ohshima M, Hashimoto S, Odagiri T, Tashiro M, Yoshikura H, Takemori T, and Tsunetsugu-Yokota Y. A subcutaneously injected UV-inactivated SARS coronavirus vaccine elicits systemic humoral immunity in mice. 2004. Int. Immunol. 16:1423-1430.

Tang L, Zhu Q, Qin E, Yu M, Ding Z, Shi H, Cheng X, Wang C, Chang G, Zhu Q, Fang F, Chang H, Li S, Zhang X, Chen X, Yu J, Wang J, and Chen Z. 2004. Inactivated SARS-CoV vaccine prepared from whole virus induces a high level of neutralizing antibodies in BALB/c mice. DNA Cell Biol. 23:391-394.

Tipnis, S R, Hooper N M, Hyde R, Karran E, Christie G, and Turner A J. 2000. A human homolog of angiotensin-converting enzyme. Cloning and functional expression as a captopril-insensitive carboxypeptidase. J. Biol. Chem. 275:33238-33243.

Van den Brink E N, Ter Meulen J, Cox F, Jongeneelen M A, Thijsse A, Throsby M, Marissen W E, Rood P M, Bakker A B, Gelderblom H R, Martina B E, Osterhaus A D, Preiser W, Doerr H W, de Kruif J, and Goudsmit J. 2005. Molecular and biological characterization of human monoclonal antibodies binding to the spike and nucleocapsid proteins of severe acute respiratory syndrome coronavirus. J. Virol. 79:1635-1644.

Yang Z Y, Kong W P, Huang Y, Roberts A, Murphy B R, Subbarao K, and Nabel G J. 2004. A DNA vaccine induces SARS coronavirus neutralization and protective immunity in mice. Nature. 428:561-564.

Zhang H, Wang G, Li J, Nie Y, Shi X, Lian G, Wang W, Yin X, Zhao Y, Qu X, Ding M, and Deng H. 2004. Identification of an antigenic determinant on the S2 domain of the severe acute respiratory syndrome coronavirus spike glycoprotein capable of inducing neutralizing antibodies. J. Virol. 78:6938-6945.

The invention claimed is:

1. A cell derived from a cell as deposited under ECACC no. 96022940, wherein the cell is engineered to express human ACE2 protein by introduction therein of a plasmid vector comprising a nucleic acid molecule encoding the human ACE2 protein.

2. The cell of claim 1 that stably expresses human ACE2 protein.

3. A method of producing a coronavirus, the method comprising the steps of:
   a) providing the cell of claim 1,
   b) culturing the cell under conditions suitable for expression of human ACE2 protein,
   c) infecting the cell with a coronavirus, and
   d) harvesting coronavirus from the medium or the cell.

4. The method according to claim 3, wherein the coronavirus is selected from the group consisting of SARS-CoV and HcoV-NL63.

5. The method according to claim 3, wherein human ACE2 protein is stably expressed in the cell.

6. The method according to claim 3, wherein the cell is capable of growing in suspension.

7. The method according to claim 3, wherein the cell can be cultured in the absence of serum.

8. The method according to claim 3, further comprising the step of inactivating or attenuating the harvested coronavirus.

9. A method for identifying a molecule capable of inhibiting a coronavirus infection and/or replication, the method comprising the steps of:
   a) incubating the cell of claim 1 with a coronavirus in the presence and absence of the candidate molecule, and
   b) determining whether the presence of the candidate molecule inhibits coronavirus infection and/or replication so as to identify a molecule capable of inhibiting a coronavirus infection and/or replication.

10. The method according to claim 9, wherein human ACE2 protein is stably expressed by the cell.

11. A method for selecting an antiviral molecule capable of reducing infection of a cell by a coronavirus, the method comprising the steps of:
   a) contacting the cell of claim 1 with a surface protein of a coronavirus in the presence or absence of a candidate antiviral molecule, the surface protein being involved in binding of the coronavirus to the human ACE2 protein expressed by the cell,
   b) measuring the binding interaction between the cell and the surface protein, and
   c) selecting a candidate antiviral molecule so that the binding interaction is reduced in comparison to the binding interaction in the absence of the candidate antiviral molecule.

12. The method according to claim 11, wherein human ACE2 protein is stably expressed by the cell.

* * * * *

UNITED STATES PATENT AND TRADEMARK OFFICE
CERTIFICATE OF CORRECTION

PATENT NO. : 7,888,102 B2  Page 1 of 1
APPLICATION NO. : 11/988146
DATED : February 15, 2011
INVENTOR(S) : Edward Norbert Van Den Brink and Jan Henrik Ter Meulen It is certified that error appears in the above-identified patent and that said Letters Patent is hereby corrected as shown below:

On the title page:
In ITEM (30) Foreign Application Priority Data    change "05106768" to --05106768.4--

Signed and Sealed this
Seventeenth Day of May, 2011

David J. Kappos
*Director of the United States Patent and Trademark Office*